United States Patent [19]

Vlock et al.

[11] Patent Number: 5,783,087

[45] Date of Patent: Jul. 21, 1998

[54] METHOD AND APPARATUS FOR ISOLATION AND PURIFICATION OF IMMUNE COMPLEXES

[75] Inventors: Daniel R. Vlock, Newton; Artin Malakian, Acton; Ingeborg Cann, Hathorne, all of Mass.

[73] Assignee: Millipore Investment Holdings Limited, Wilmington, Del.

[21] Appl. No.: 921,106

[22] Filed: Aug. 29, 1997

Related U.S. Application Data

[63] Continuation of Ser. No. 225,162, Apr. 8, 1994, abandoned.

[51] Int. Cl.$^6$ .................... B01D 21/26; B01D 61/14

[52] U.S. Cl. .................... 210/651; 210/650; 210/781; 210/782; 210/787; 210/806; 436/177; 436/178; 494/36; 494/37

[58] Field of Search .................... 210/650, 651, 210/653, 654, 655, 806, 781, 782, 787, 789, 321.67, 321.68, 515, 516, 518, 512.1; 422/72, 101, 102; 436/531, 532, 538, 45, 177, 178; 530/412, 815, 816, 812, 413, 414; 494/36, 37; 435/30

[56] References Cited

U.S. PATENT DOCUMENTS

| 3,888,629 | 6/1975 | Bagshawe . | |
|---|---|---|---|
| 4,154,795 | 5/1979 | Thorne | 422/102 |
| 4,350,594 | 9/1982 | Kawai et al. | 210/637 |
| 4,663,049 | 5/1987 | Kolff et al. | 210/651 |
| 4,705,753 | 11/1987 | Gregor et al. | 435/180 |
| 4,832,851 | 5/1989 | Bowers et al. | 210/650 |
| 5,003,047 | 3/1991 | Yarmush et al. | 530/413 |
| 5,112,490 | 5/1992 | Turpen | 210/650 |
| 5,116,496 | 5/1992 | Scott | 210/455 |
| 5,124,041 | 6/1992 | Sheer et al. | 210/641 |
| 5,259,951 | 11/1993 | Arrighi et al. | 210/781 |
| 5,264,184 | 11/1993 | Aysta et al. | 422/101 |
| 5,288,415 | 2/1994 | Chen-Wu et al. | 210/781 |

FOREIGN PATENT DOCUMENTS

| 0127737 | 12/1984 | European Pat. Off. . |
| 0248524 | 12/1987 | European Pat. Off. . |
| 0505118 | 9/1992 | European Pat. Off. . |
| 0569115 | 11/1993 | European Pat. Off. . |
| 0588564 | 3/1994 | European Pat. Off. . |
| 2330694 | 6/1977 | France . |
| 85/01941 | 5/1985 | WIPO . |
| 91/07648 | 5/1991 | WIPO . |

OTHER PUBLICATIONS

Daniel. R. Vlock et al.; "Purification and partial characterization of a shed 66 kDa melanoma–associated antigen identified by autologous antibody", *Biochemica et Biophysica Acta*.1080 (1991); pp. 1–10.

Daniel R. Vlock et al.; "Isolation and Partial Characterization of Melanoma–associated Antigens Identified by Autologous Antibody"; *Journal of Clinical Investigation*; vol. 81, Jun. 1988; pp. 1746–1751.

Anders Christensson et al.; "Serum Prostate Specific Antigen Complexed to α1–Antichymotrypsin as an indicator of Prostate Cancer"; *The Journal of Urology*; vol. 150, Jul. 1993; pp. 100–105.

Daniel R. Vlock et al.; "Serial Studies of autologous antibody reactivity to squamous cell carcinoma of the head and neck"; *Cancer Immunology Immunotherapy*No. 34 (1992); pp. 329–336.

(List continued on next page.)

*Primary Examiner*—John Kim
*Attorney, Agent, or Firm*—Nields, Lemack & Dingman

[57] ABSTRACT

A system and method for isolating and purifying complexes of biologically active compounds. The inventive system and method utilize a centrifugal filtration device employing a membrane having ligands that preferentially bind a biologically active compound. An advantage of the invention is that purifications of, e.g., immune complexes, which heretofore took up to five days to carry out, may now be done in as little as two hours.

8 Claims, 1 Drawing Sheet

OTHER PUBLICATIONS

Daniel R. Vlock et al.; "Incidence of Serum Antibody Reactivity to Autologous Head and Neck Cancer Cell Lines and Augumentation of Antibody Reactivity following Acid Dissociation and Ultrfiltration"; *Cancer Research* 49, Mar. 15, 1989; pp. 1361–1365.

Daniel R. Vlock et al.; "Clinical Correlates of Circulating Immune Complexes and Antibody Reactivity in Squamous Cell Carcinoma of the Head and Neck": *Journal of Clinical Oncology*; vol. 11, No. 12 (Dec.), 1993; pp. 001–007.

Daniel R. Vlock; "Immune Complexes and Malignancy"; in *Immunodiagnosis of Cancer*, 2nd ed; R. B. Herberman, D. W. Mercer, eds.; 1991; pp. 555–586.

Millipore Corporation Brochure: "What this centrifugal filter pulls out of a small volume sample . . . "; *Ultrafree–MC DEAE Centrifugal Filter*; 1994; pp. 1–2.

Amicon Technical Data Sheet: "Create your own Immunoaffinity Device with MAC™Active Membrane Capsules And Discs"; Publication No. 193, 1992.

METHOD AND APPARATUS FOR ISOLATION AND PURIFICATION OF IMMUNE COMPLEXES

This application is a continuation of application Ser. No. 08/225,162 filed Apr. 8, 1994 (abandoned).

FIELD OF THE INVENTION

This invention relates to methods and apparatus for isolating and purifying biologically active compound complexes, such as immune complexes, from their native fluids, which are faster and more sensitive than methods disclosed up to this point.

BACKGROUND OF THE INVENTION

It has long been desired to purify and characterize biologically active compounds from their native fluids, e.g., blood serum. Examples of such compounds are enzymes, nucleic acids, antigens, and antibodies, as well as complexes thereof, such as immune complexes (i.e., antigen-antibody pairs). As noted in Daniel R. Vlock, in *Immune Complexes and Malignancy*, in *Immunodiagnosis of Cancer*, 2 $_{nd}$ Ed., ed. R. B. Herberman et al. (1991; New York: Marcel Dekker, Inc.), immune complexes have been implicated in a number of disease states. Their roles in autoimmune diseases, glomerulonephritis, infectious diseases, and neoplasia have been under investigation for over 20 years. Although there has been a large body of literature describing immune complexes in cancer, the role of immune complexes in malignancy is incompletely understood.

Technical difficulties encountered in the detection of immune complexes have hampered their evaluation. Tests for immune complexes should be sensitive, specific, and reproducible. We have noted that by dissociating immune complexes through acidification and microfiltration of the patient's sera, we have been able to significantly augment the incidence and titer of these antibodies. Subsequent studies have demonstrated correlations with antibody titer and clinical course. Our previous methodology used a standard ultrafiltration chamber fitted with a 100,000 MW cutoff membrane. A drawback of this technique, however, is that it takes between 48 and 72 hours to process a single serum specimen.

This difficulty in purifying and characterizing other biologically active compounds is by no means limited to immune complexes. Conventional purification and characterization means, e.g., affinity separations on gels or membranes, or liquid chromatography, is not only too slow but is also not sensitive enough and typically results in poor recovery. In membrane applications it is important to control the rate of fluid passage through the membrane to allow the biologically active compound or complex to bind. This is difficult to do, however, if using conventional means to move the fluid through the membrane, such as pressure or vacuum, and highly impractical to make inexpensive, disposable devices using the pressure or vacuum design principle. The equipment used employing these conventional techniques also requires more skill and effort to perform the analyses than is desirable. Also, such existing methods are not easily adaptable for multi-sample processing, or to automation. It is therefore an object of this invention to provide a simple, reproducible and inexpensive method for isolating and purifying biologically active compound complexes and components thereof from serum (and an device for doing so) that is faster than prior methods, but with no loss in sensitivity or yield.

SUMMARY OF THE INVENTION

The invention relates to a method of purifying biologically active compound complexes comprising the steps of a) providing a centrifugal device for preferentially removing such complexes from a fluid, the device comprising at least one capture unit comprising an upper chamber for receiving fluid to be treated; a lower chamber in fluid communication with the upper chamber, for receiving filtrate; and a porous capture membrane layer disposed between the upper and lower chambers, the membrane layer having ligands for preferentially binding a biologically active compound; b) adding a fluid sample to the upper chamber and centrifuging the device to produce a filtrate; c) removing the filtrate from the lower chamber; d) treating the porous capture membrane layer with an eluting solvent which promotes the dissociation of the complex into its components so as to elute the components off the membrane layer; e) centrifuging the device to produce a second filtrate; f) transferring the second filtrate to a separation device having an upper chamber for receiving fluid to be treated; a lower chamber in fluid communication with the upper chamber, for receiving filtrate; and an ultrafiltration membrane layer disposed therebetween that is sized to allow at least one component of the complex to pass through; and g) centrifuging the separation device to produce a third filtrate.

The invention further relates to a system for preferentially removing biologically active compound complexes from a fluid comprising a) a centrifugal device comprising at least one capture unit comprising an upper chamber for receiving fluid to be treated; a lower chamber in fluid communication with the upper chamber, for receiving filtrate; and a porous capture membrane layer disposed between the upper and lower chambers, the membrane layer having ligands for preferentially binding a biologically active compound, and b) a separation device comprising an upper chamber for receiving fluid to be treated; a lower chamber in fluid communication with the upper chamber, for receiving filtrate; and an ultrafiltration membrane layer disposed between the upper and lower chambers, the membrane layer sized to allow at least one component of the complex to be filtered through.

DESCRIPTION OF THE INVENTION

Figure 1:
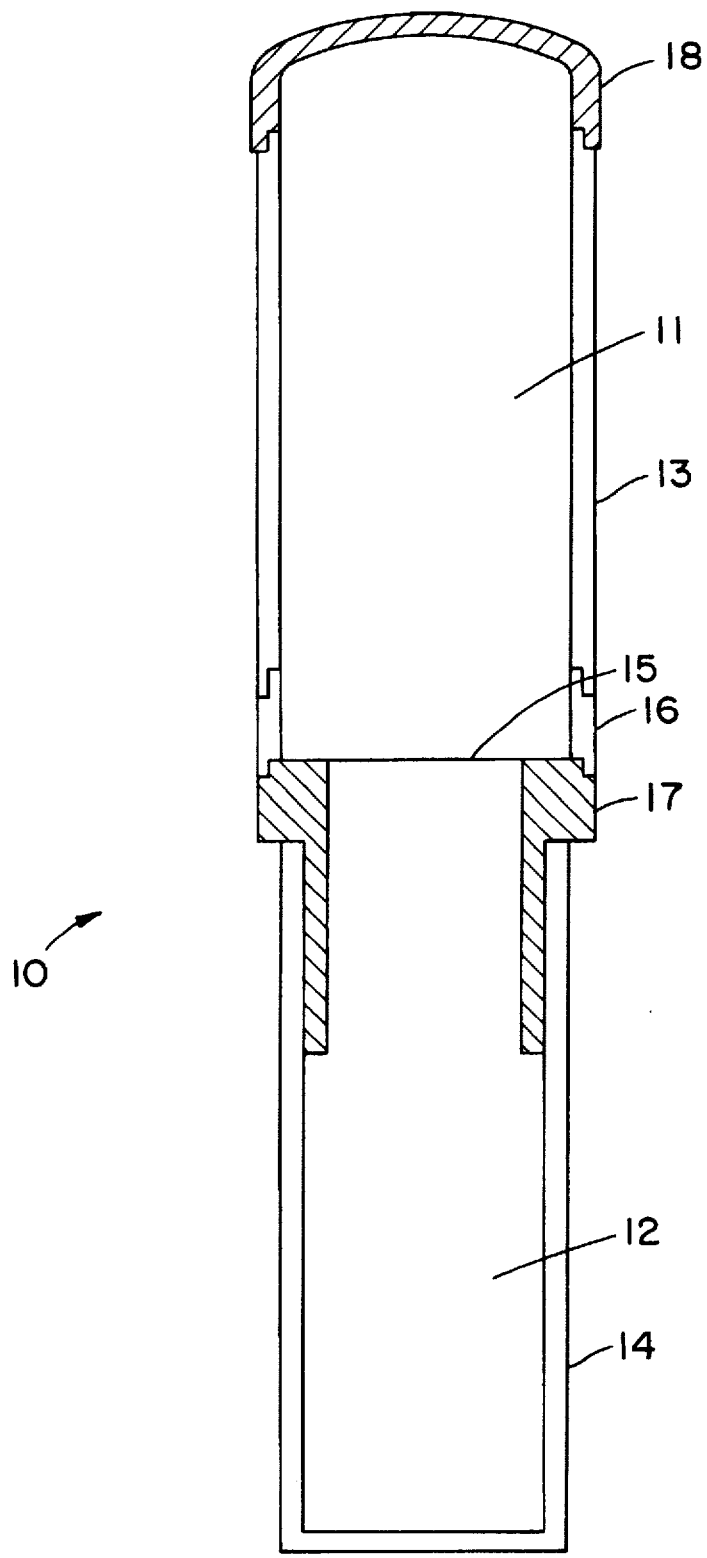
FIG. 1 depicts an embodiment of a device according to the invention, in longitudinal cross-section.

Our invention relates to methods and systems for purifying biologically active compound complexes. A surprising advantage of our invention is that purifications of, e.g., immune complexes, which until now took up to five days to carry out, may now be done in as little as two hours.

An exemplary embodiment of a device for use in the invention is shown in longitudinal cross-section in FIG. 1. Device 10 (hereinafter termed "centrifugal device") comprises upper chamber 11, into which fluid sample to be processed is placed. Upper chamber 11 is defined by the substantially cylindrical wall 13. At the upper edge of wall 13 is found cap 18, which protects the contents of upper chamber 11. Cap 18 can be, e.g., snap fit on or attached by a screw thread. At the lower edge of wall 13 is a capture membrane locking sleeve 16, which securely sandwiches capture membrane layer 15 between the interlocking locking sleeve 16 and chamber end cap 17. Capture membrane layer 15 thus forms a semi-permeable barrier between upper chamber 11 and lower chamber 12, which has a closed end to form a fluid receptacle. The membrane may also be secured by other conventional means, e.g., by using an o-ring.

Chamber end cap 17 is designed to frictionally fit into cup 14, which defines lower chamber 12. In this manner the entire unit may be placed into a centrifuge shield for centrifugation. When device 10 is spun in the centrifuge, fluid sample is pulled from upper chamber 11 to lower chamber 12 through capture membrane layer 15. The filtrate thus produced in cup 14 may then be decanted by detaching the cup.

The capture membrane layer is a porous membrane having ligands for preferentially binding a biologically active compound (and, thus, the complex of which the compound is a component). (The word "membrane" as used herein is meant to not only refer to true "membranes", but to all forms of porous planar filter media, e.g., papers, etc.) The capture membrane material may be any material suited to this purpose; the membranes, and means for coupling ligands to ("activating") the membranes are well-known, for example, cellulosic, nylon, and polysulfone membrane materials. The nature of the membrane is important inasmuch as it should be fairly inert with respect to the solvents used, and the biologically active compounds of interest, and must allow for the ligand attachment. The pore size of the membrane material is dependent on the particular biologically active compound sought to be isolated, but, in general, the average pore size must be at least large enough to allow unwanted components to pass through the membrane layer. Membrane materials that we have found useful, while not intended to be limiting, may be found in Table I. Microfiltration and ultrafiltration ("UF") type membranes are preferred, with microfiltration membranes particularly preferred.

TABLE I

| Membrane Name* | Membrane Type | MWCO† | Classification |
| --- | --- | --- | --- |
| YC05 | Cellulosic | 500 | Ultrafiltration |
| YM1 | " | 1000 | " |
| YM3 | " | 3000 | " |
| YM10 | " | 10000 | " |
| YM30 | " | 30000 | " |
| YM100 | " | 100000 | " |
| PM10 | Polysulfone | 10000 | " |
| PM30 | " | 30000 | " |
| XM50 | DYNEL ™ | 50000 | " |
| XM300 | " | 300000 | " |
| GLS.2 | Polysulfone | 0.2μ‡ | Microfiltration |
| GLS.45 | " | 0.45μ‡ | " |
| "Bio-38" | Cellulosic | 5μ‡ | " |

*AMICON, INC., BEVERLY, MASS.
†molecular weight cutoff
‡avg. pore size

The more important factor in selecting a capture membrane layer is the biologically active compounds themselves, because the nature of the compounds will most determine a) the particular ligand to be attached to the membrane and b) the membrane material to be used. The choice of ligand is more important because the complex will not bind to the membrane otherwise. Exemplary ligands are shown in Table II. Other ligands, or combinations thereof, may be arrived at by those of ordinary skill in the art.

TABLE II

| Ligand |
| --- |
| protein A |
| protein G |
| lectins |
| antibodies |
| antigens |
| chiral moieties |
| strep-avidin |
| biological complexes |
| α-chymotrypsin |
| nucleic acids |

The capture membrane layer may preferably comprise one or more sheets of membrane, one laid on top of the other. This is particularly advantageous, because several sheets of membrane laid on top of each other increase the capacity for the biologically active compound on the membrane, and enhance mass transfer and opportunity for binding of the biologically active compound to the capture membrane layer.

The isolation or purification of biologically active compound complexes according to our invention may be carried out as follows. Fluid, for example, blood serum, containing the biologically active compound complex(es) of interest is first placed into the upper chamber of the centrifugal device generally described above. The device is then placed into a centrifuge and spun for a time and speed sufficient to move the fluid component from the upper chamber through the capture membrane and into the lower chamber, thus producing a filtrate. The biologically active complex(es) will preferentially bind to the membrane. The optimal centrifuge time and speed used may be chosen without much effort; at too high a speed, it can be anticipated that some of the biologically active compounds of interest, passing through the membrane too quickly, will not bind and will be lost in the filtrate. It is therefore advisable to use a slower speed initially and gradually work the speed up in subsequent runs if desired. The centrifugal device only needs to be spun long enough to remove liquid from the upper chamber; when employing an ultrafiltration membrane, however, the membrane must be left moistened. Temperature-sensitive samples may be processed in a temperature controlled centrifuge environment if necessary.

The device may then be removed and the capture membrane preferably washed to remove unbound compounds, with one or several volumes (each wash volume preferably roughly equal to the fluid capacity of the upper chamber) of, e.g., DI water or a neutral buffer solution, with centrifugation following each wash. The filtrate and washes may be saved or discarded as necessary by detaching the cup on the bottom of the unit, decanting the fluid and reattaching the cup. After this, the capture membrane is treated with an eluting solvent as described below.

An example of how certain immune complexes may be isolated and purified from blood serum is as follows. The complexes may be purified and concentrated on a capture membrane layer having protein A ligands. After the first centrifugation step, the capture membrane layer is treated with an eluting solvent such as acidic buffer solutions, e.g., pH 2.5–3.5; salt solutions; and solutions containing competitive substrates. A particularly preferred eluting solvent is an acidic (e.g., glycine-saline buffer, pH 2.5–3.5) solution, which causes dissociation of the immune complex into its components, antigen and antibody. Dissociation also removes the immune complex from the capture membrane.

The buffer pH should be low enough to dissociate the immune complex components from each other, but not so low as to denature them or damage the capture membrane.

After the immune complex components are eluted by centrifugation, the filtrate in the lower chamber is then transferred to a second device, hereinafter termed "separation device", which is substantially of the same design as that in FIG. 1, but comprising an membrane (preferably an ultrafiltration membrane) sized to preferentially allow one of the immune complex components to pass through. Examples of membranes that may be used are shown in Table I, above. Those of ordinary skill in the art will know how to select an appropriate membrane/MWCO/average pore size, but we have found that a ultrafiltration membrane with a MWCO of 100,000, e.g., AMiCONO®YM100, is preferable for most purposes. Once the sample containing the dissociated immune complex components is transferred to the separation device upper chamber, the separation device is then centrifuged under conditions as described above to separate the components. The individual components may be easily assayed thereafter.

It should be noted that the embodiment of the device described above may be reconfigured into many different embodiments and combinations. Likewise, the method of the invention may be employed in combination with other analytical tools to achieve a particular end. For example, the device described above could be configured from a single tube-type apparatus into a unitary plate containing an 8×12 array of "upper chamber" wells (i.e., in the standard 96 well plate configuration) in order to use the variety of equipment and methodologies, e.g., centrifuges, plate readers, that support the format. Continuing further with this example, this "capture plate" would snap onto or otherwise cooperatively attach to a standard 96 well plate to allow individual centrifugal isolation or purification as previously described herein. Furthermore, capture plates having different capture membrane layers specific for different biologically active compounds could be stacked on top of one another to isolate each biologically active compound from the other, thus reducing several separations to one. In another embodiment along these lines, the bottommost capture plate could be made having capture membranes in each well which may be used for membrane-bound ELISA assays.

The device described in FIG. 1 above could also be configured to stack "upper chamber" units in one "single-position" device to isolate different biologically active compounds from a fluid in one step, as in the 96 well capture plate just described. Such a capture device would have a greater capacity for each biologically active compound, and, with an appropriate variety of capture membranes, would allow the researcher to custom configure a device for his or her own requirements. The advantage that all these 'stackable' embodiments of our invention share over current affinity membrane methods, i.e., vacuum, positive pressure or gravity pull through the membrane, is that the force pulling the sample through the membrane will be equal in each "upper chamber", which is critical for ensuring equality of mass transfer, and thus consistency of biologically active compound retention, over each capture membrane in the device.

One further convenient advantage of the embodiment shown in FIG. 1 is that elution of the biologically active compound(s) retained on the membrane may be done by inverting the unit, adding eluting solvent to the receptacle formed by the cylindrical wall of chamber end cap 17, and centrifuging the inverted unit so as to elute into the cap 18.

What is claimed is:

1. A method of separating intact immune complexes from cellular debris comprising the steps of a) providing a first centrifugal device for removing said complexes from a fluid, said device comprising at least one capture unit comprising 1) an upper chamber for receiving fluid to be treated; 2) a lower chamber in fluid communication with said upper chamber, for receiving filtrate; 3) a porous immune-affinity membrane layer, said porous immune-affinity membrane layer selected from the group consisting of microfiltration and ultrafiltration membranes, disposed between said upper and lower chambers, said porous immnune-affinity membrane layer having ligands attached thereto for binding said immune complexes;

b) adding a fluid sample to said upper chamber and centrifuging said first centrifugal device to produce a filtrate;

c) removing said filtrate from said lower chamber;

d) eluting said complex off said porous immune-affinity membrane layer by treating said porous immune-affinity membrane layer with an eluting solvent that promotes the dissociation of said complex into its components;

e) centrifuging said first centrifugal device to produce a second filtrate;

f) transferring said second filtrate to a second separation device having 1) an upper chamber for receiving said second filtrate; 2) a lower chamber in fluid communication with said upper chamber, for receiving a third filtrate; and 3) an ultrafiltration membrane layer disposed therebetween that is sized to allow at least one of said components to pass through; and g) centrifuging said second separation device to produce a third filtrate.

2. The method of claim 1 wherein said eluting solvent is selected from the group consisting of acidic buffer solutions, salt solutions, and solutions containing competitive substrates.

3. The method of claim 1 wherein said immune-affinity membrane layer comprises a plurality of membranes in a stack.

4. The method of claim 1 wherein said immune-affinity membrane layer of said first centrifugal device is of the microfiltration type.

5. The method of claim 1 wherein said immnune-affinity membrane layer is selected from the group consisting of cellulosic, nylon, and polysulfone membrane materials.

6. The method of claim 1 wherein said ligands are selected from the group consisting of protein A, protein G, lectins, antibodies, antigens, chiral moieties, strep-avidin, biological complexes, α-chymotrypsin, nucleic acids, and combinations thereof.

7. The method of claim 1 wherein said first centrifugal device comprises a plurality of capture units.

8. The method of claim 7 wherein said capture units are laid out in a planar 8×12 array.

* * * * *